US012572133B2

(12) United States Patent (10) Patent No.: US 12,572,133 B2
Sinha et al. (45) Date of Patent: Mar. 10, 2026

(54) PREDICTIVE MOTION MAPPING FOR FLEXIBLE DEVICES

(71) Applicant: KONINKLIJKE PHILIPS N.V., Eindhoven (NL)

(72) Inventors: Ayushi Sinha, Baltimore, MD (US); Molly Lara Flexman, Melrose, MA (US); Grzegorz Andrzej Toporek, Cambridge, MA (US); Ashish Sattyavrat Panse, Burlington, MA (US); Jochen Kruecker, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 203 days.

(21) Appl. No.: 18/266,621

(22) PCT Filed: Dec. 7, 2021

(86) PCT No.: PCT/EP2021/084464
§ 371 (c)(1),
(2) Date: Jun. 12, 2023

(87) PCT Pub. No.: WO2022/128589
PCT Pub. Date: Jun. 23, 2022

(65) Prior Publication Data
US 2024/0045404 A1 Feb. 8, 2024

Related U.S. Application Data

(60) Provisional application No. 63/126,263, filed on Dec. 16, 2020.

(30) Foreign Application Priority Data

May 14, 2021 (EP) ..................................... 21173896

(51) Int. Cl.
*G05B 19/4155* (2006.01)
*A61B 34/20* (2016.01)
(Continued)

(52) U.S. Cl.
CPC .......... *G05B 19/4155* (2013.01); *A61B 34/20* (2016.02); *A61B 34/37* (2016.02);
(Continued)

(58) Field of Classification Search
CPC ...... G05B 19/4155; G05B 2219/50391; A61B 34/20; A61B 34/37; A61B 2034/2055;
(Continued)

(56) References Cited

U.S. PATENT DOCUMENTS 10,454,347 B2 10/2019 Covington
11,497,382 B1* 11/2022 Ikuta .................. A61B 1/00096
(Continued)

OTHER PUBLICATIONS

Shape Prediction Algorithm for Flexible Endoscope, May 31-Jun. 7, 2014, 2014 IEEE International Conference on Robotics & Automation, Hong Kong Convention and Exhibition Center, pp. 2856-2861 (Year: 2014).*

(Continued)

*Primary Examiner* — Sze-Hon Kong

(57) ABSTRACT

A controller (150) for interventional medical devices includes a memory (151) and a processor (152). The memory (151) stores instructions that the processor (152) executes. When the instructions are executed, the instructions cause the controller (150) to obtain at least one location of a distal end of the interventional medical device (101), identify motion at a proximal end of an interventional medical device (101), apply a first trained artificial intelligence to the motion at the proximal end of the interventional medical device (101) and to the at least one location of the distal end of the interventional medical device (101), and (Continued)

predict motion along the interventional medical device (101) towards a distal end of the interventional medical device (101) during the interventional medical procedure. The controller (150) also obtains images of the distal end of the interventional medical device (101) from a medical imaging system (120) to determine when the actual motion deviates from the predicted motion.

17 Claims, 10 Drawing Sheets

(51) Int. Cl.
| | |
|---|---|
| *A61B 34/37* | (2016.01) |
| *G06T 7/246* | (2017.01) |
| *G06T 7/73* | (2017.01) |
| *A61B 34/30* | (2016.01) |

(52) U.S. Cl.
CPC ............... *G06T 7/248* (2017.01); *G06T 7/74* (2017.01); *A61B 2034/2055* (2016.02); *A61B 2034/301* (2016.02); *G05B 2219/50391* (2013.01); *G06T 2207/10121* (2013.01); *G06T 2207/20021* (2013.01); *G06T 2207/20081* (2013.01); *G06T 2207/20084* (2013.01); *G06T 2207/30004* (2013.01)

(58) Field of Classification Search
CPC ..... A61B 2034/301; G06T 7/248; G06T 7/74; G06T 2207/10121; G06T 2207/20021; G06T 2207/20081; G06T 2207/20084; G06T 2207/30004; G06T 2207/10132; G06T 2207/30021; G06T 7/20
See application file for complete search history.

(56) References Cited

U.S. PATENT DOCUMENTS

| | | | |
|---|---|---|---|
| 2008/0160489 A1 | 7/2008 | Bruijns | |
| 2017/0312481 A1 | 11/2017 | Covington et al. | |
| 2018/0177556 A1 | 6/2018 | Noonan | |
| 2019/0239723 A1 | 8/2019 | Duindam et al. | |
| 2020/0364865 A1* | 11/2020 | Donhowe | A61B 1/0016 |
| 2021/0052140 A1* | 2/2021 | Tata | A61B 5/067 |
| 2022/0142712 A1 | 5/2022 | Toporek | |
| 2022/0175269 A1* | 6/2022 | Lu | A61B 5/6851 |
| 2022/0258333 A1* | 8/2022 | Gao | B25J 9/106 |
| 2023/0372014 A1* | 11/2023 | Gao | A61B 34/20 |
| 2024/0008916 A1* | 1/2024 | Mei | A61B 18/1477 |
| 2024/0285363 A1* | 8/2024 | Adebar | A61B 34/20 |
| 2024/0325098 A1* | 10/2024 | Itkowitz | A61B 34/35 |
| 2024/0407873 A1* | 12/2024 | Diolaiti | A61B 90/37 |

OTHER PUBLICATIONS

Li et al., "Deep learning for haptic feedback of flexible endoscopic robot without prior knowledge on sheath configuration", International Journal of Mechanical Sciences 163 (2019) 105129.
Li et al., "Distal-end force prediction of tendon-sheath mechanisms for flexible endoscopic surgical robots using deep learning", Mechanism and Machine Theory, 134 (2019) pp. 323-337.
International Search report and Written Opinion of PCT/EP2021/084464, dated Apr. 4, 2022.

* cited by examiner

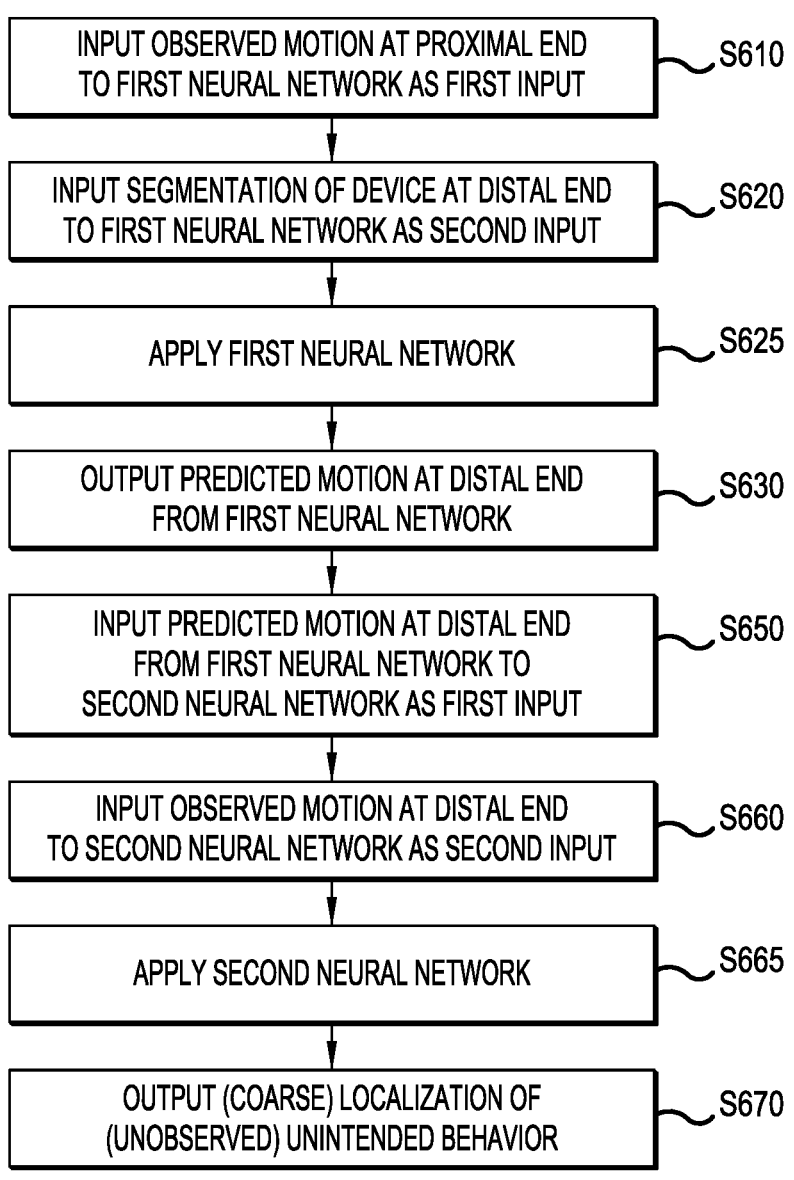

INPUT OBSERVED MOTION AT PROXIMAL END
TO FIRST NEURAL NETWORK AS FIRST INPUT ⟩ S610

INPUT SEGMENTATION OF DEVICE AT DISTAL END
TO FIRST NEURAL NETWORK AS SECOND INPUT ⟩ S620

APPLY FIRST NEURAL NETWORK ⟩ S625

OUTPUT PREDICTED MOTION AT DISTAL END
FROM FIRST NEURAL NETWORK ⟩ S630

INPUT PREDICTED MOTION AT DISTAL END
FROM FIRST NEURAL NETWORK TO
SECOND NEURAL NETWORK AS FIRST INPUT ⟩ S650

INPUT OBSERVED MOTION AT DISTAL END
TO SECOND NEURAL NETWORK AS SECOND INPUT ⟩ S660

APPLY SECOND NEURAL NETWORK ⟩ S665

OUTPUT (COARSE) LOCALIZATION OF
(UNOBSERVED) UNINTENDED BEHAVIOR ⟩ S670

FIG.6C

PREDICTIVE MOTION MAPPING FOR FLEXIBLE DEVICES

CROSS-REFERENCE TO PRIOR APPLICATIONS

This application is the U.S. National Phase application under 35 U.S.C. § 371 of International Application No. PCT/EP2021/084464 filed on Dec. 7, 2021, which claims the benefit of European Patent Application No. 21173896.8, filed May 14, 2021 and U.S. Provisional Application No. 63/126,263, filed on Dec. 16, 2020. These applications are hereby incorporated by reference herein.

BACKGROUND

Use of tools on anatomy in minimally invasive procedures can be challenging when live medical imaging does not show unexpected motion of the tools. For some tools, motion introduced at the proximal ends sometimes does not produce corresponding motion along the lengths of the tools and at the distal ends of the tools. Unexpected motion along the lengths of the tools includes sideways translation and buckling. Variation in the motion is dependent on types of the tools, anatomies of the patients, and curvature along the lengths of the tools. The unexpected motion of the tools may also be due to tool characteristics such as dimensions, flexibility, torque transmission, and friction. A result of unintended motion may be an adverse contact with tissue such as a vessel dissection or perforation. As an example, unexpected motion may result from motion introduced at the proximal end of a long and thin tool such as a catheter or guidewire.

When the minimally invasive procedure is performed under the guidance of two-dimensional (two-dimensional) fluoroscopy, aspects of three-dimensional (three-dimensional) motion of the tools may be missed. Often only the distal end of the tool is within the fluoroscopy field of view (FOV), and therefore, any motion along the length of the tool that is outside the FOV is not perceived. Further, motion in the distal end may often also not be perceived due to foreshortening in the fluoroscopy imaging. Therefore, large motions at the proximal end of a tool often do not result in perceived motion in the distal end, while resulting in unexpected behavior along the length of the tool. A specific example of this problem occurs when performing peripheral vascular navigation in the leg. The catheter and guidewire are navigated from the femoral access, over the iliac horn, and down the contralateral femoral artery. The x-ray image following the tool loses sight of the iliac horn crossover where tools may buckle back up into the aorta.

Conventionally, given a start of a course of a tool and an end of the course of the tool, the course may be plotted by modeling a micro-catheter with a micro-catheter tube following a micro-catheter centerline, and by assuming that the micro-catheter centerline is composed of an alternating sequence of straight-lines and curves. However, interference from external forces such as physician manipulation of the catheter is not accounted for.

Predictive motion mapping for flexible devices as described herein addresses concerns as described above.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

FIG. 6C illustrates a method for predictive motion mapping for flexible devices, in accordance with a representative embodiment.

DETAILED DESCRIPTION

Figure 1:
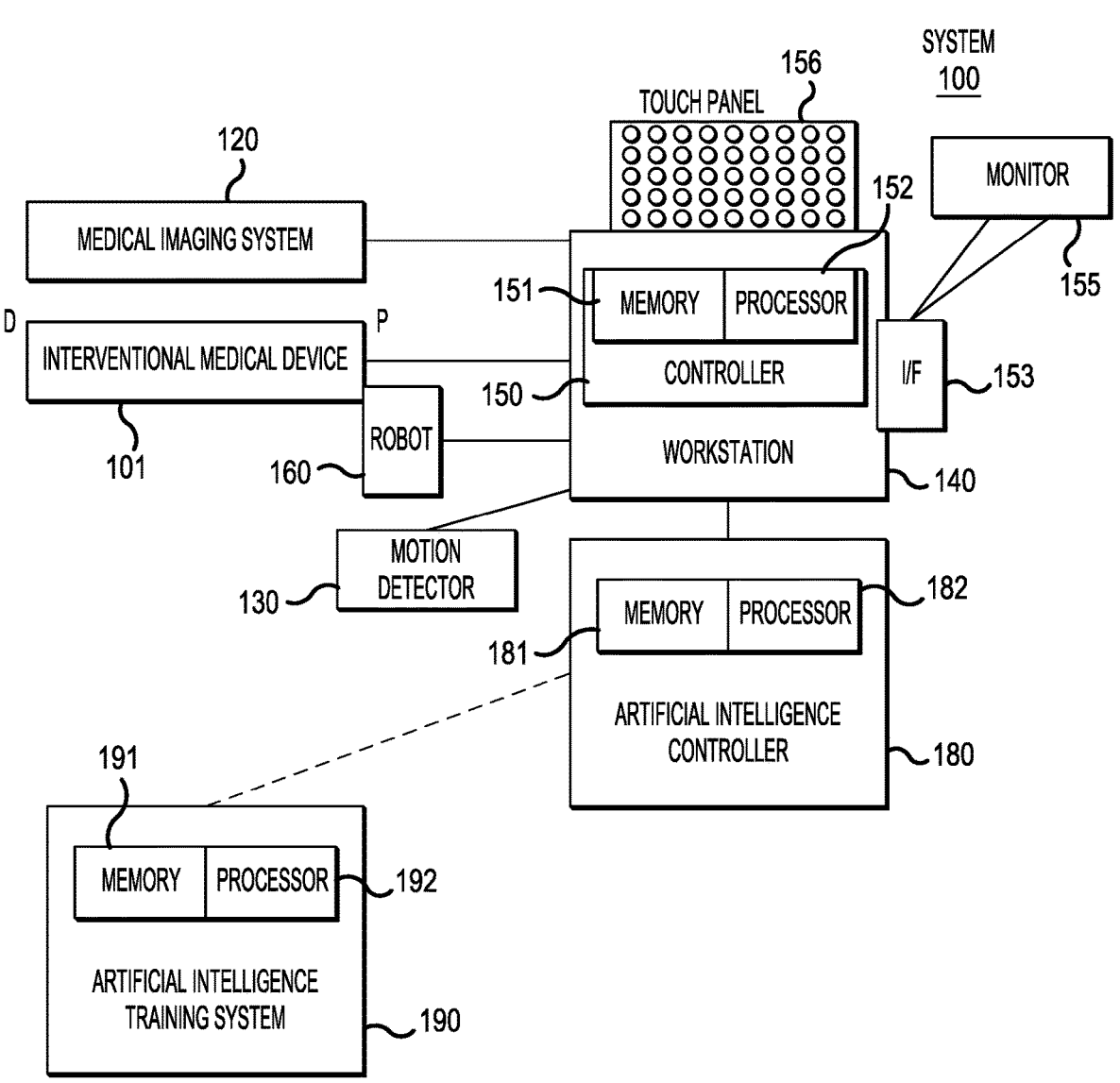
FIG. 1 illustrates a system for predictive motion mapping for flexible devices, in accordance with a representative embodiment.

In the following detailed description, for the purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

The present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

As described herein, a range of motion that can be expected at the distal end of an interventional medical device may be predicted from particular motion at the proximal end of the interventional medical device. Expected motions along the length of the interventional medical device visible in the fluoroscopy FOV may be predicted, and alerts may be raised when observed motions are outside the range of expected motions. Further, based on observed unexpected motion, potentially unintended behavior outside the fluoroscopy FOV may be predicted. The warnings produced by this system may prevent accidental damage to vessels and other undesired outcomes. Predictive motion mapping for flexible devices may be used to track motion of interventional medical devices and to predict predicted coarse localizations to coarsely localize unintended behavior of the interventional medical devices even for parts of the interventional medical devices that are not within FOVs of medical imaging systems used during interventional medical procedures.

FIG. 1 illustrates a system for predictive motion mapping for flexible devices, in accordance with a representative embodiment.

In FIG. 1, a control system 100 is shown along with an interventional medical device 101. The interventional medical device 101 has proximal end P nearest the control system 100 and a distal end D furthest from the control system 100. The distal end D may correspond to a the portion of the interventional medical device 101 that is first inserted into the anatomy of a patient in an interventional medical procedure.

The control system 100 includes a medical imaging system 120, a motion detector 130, a workstation 140, a robot 160, and an artificial intelligence controller 180. The workstation 140 includes a controller 150, an interface 153, a monitor 155 and a touch panel 156. The controller 150 includes a memory 151 that stores instructions and a processor 152 that executes the instructions. The interface 153 interfaces the monitor 155 to a main body of the workstation 140. The artificial intelligence controller 180 includes a memory 181 that stores instructions and a processor 182 that executes the instructions to implement one or more aspects of methods described herein.

Characteristics of the interventional medical device 101 may affect how the interventional medical device 101 moves, both in terms of expected motion and unexpected and/or unintended motion. For example, a floppy guidewire may behave differently than a stiff guidewire, both in terms of expected motion and unexpected and/or unintended motion. Accordingly, characteristics of the interventional medical device 101 may be used as a basis or one of multiple bases of compensating for the unintended motion. Examples of an interventional medical device 101 include a guidewire, a catheter, a microcatheter and a sheath.

The medical imaging system 120 may be an interventional X-ray imaging system. An interventional X-ray imaging system may include an X-ray tube adapted to generate X-rays and an X-ray detector configured to acquire time-series X-ray images such as fluoroscopy images. Examples of such X-ray imaging systems include digital radiography-fluoroscopy systems such as ProxiDiagnost from Philips, fixed C-arm X-ray systems such as Azurion from Philips, and mobile C-arm X-ray systems such as Veradius from Philips.

The medical imaging system 120 may be provided with an image processing controller that is configured to receive fluoroscopy images acquired during the interventional medical procedure and output a segmentation of the interventional device. An image processing controller may be implemented by/as the controller 150 shown in FIG. 1, or may be implemented by/as another controller directly integrated with the medical imaging system 120.

Segmentation for images produced by the medical imaging system 120 produces a representation of the surface of structures such as anatomical features and the interventional medical device 101. The segmented representations may consist for example of sets of points in three-dimensional (3-D) coordinates on the surfaces of the structures, and triangular plane segments defined by connecting neighboring groups of three points, such that the entire structures are covered by meshes of non-intersecting triangular planes. A three-dimensional model of the interventional medical device 101 may be obtained by segmenting. A segmentation may also be represented as a binary mask, (x,y) coordinates of the interventional medical device 101 in image space, a two-dimensional spline or a wireframe model. Segmentation may be computed by thresholding, template matching, active contour modeling, neural network based segmentation methods, and other segmentation methods. Segmenting may be provided for X-ray imagery generated by an X-ray imaging system or a three-dimensional ultrasound volume generated by an ultrasound imaging system.

The robot 160 may be used to control movement of the interventional medical device 101 under the control of an operator. Motion at the proximal end of the interventional medical device 101 may be detected from the motion of the robot 160 when the robot 160 controls the interventional medical device 101.

The artificial intelligence controller 180 may include multiple controllers, and may implement first artificial intelligence and second artificial intelligence as described herein. Artificial intelligence implemented by the artificial intelligence controller 180 may result from training in a dedicated training environment. The artificial intelligence controller 180 may be provided entirely separately from the other components of the control system 100 in FIG. 1.

The artificial intelligence controller 180 may be a neural network controller and may be used during an application phase during an interventional medical procedure. The artificial intelligence controller 180 is configured to receive motion information at the proximal end of interventional medical device 101. The artificial intelligence controller 180 is also configured to receive fluoroscopy images of and/or a segmented representation of the interventional medical device 101 in fluoroscopy images from the medical imaging system 120. The artificial intelligence controller 180 may also receive a type of the interventional medical device 101, such as from a drop-down menu provided via the monitor 155 or from automatic detection of the interventional medical device 101. The interventional medical device may be automatically detected using object detection and classification from images of the interventional medical device 101 captured by operating room cameras before the interventional medical device 101 is inserted into the patient on images captured. The artificial intelligence controller 180 may optionally operate based on constraints derived from the fluoroscopy images and/or segmented representations of the interventional medical device 101. Constraints that may also be used as input by the artificial intelligence controller include length of the interventional medical device 101, maximum allowed curvature of the interventional medical device 101, and motion predicted and/or observed along the length of the interventional medical device 101 visible in the fluoroscopy FOV.

A result of applying the first artificial intelligence and second artificial intelligence by the artificial intelligence controller 180 may be a prediction of a coarse localization of where unexpected behavior such as buckling outside of the fluoroscopy FOV may be occurring based on the disagreement between predicted and observed motion within the fluoroscopy FOV. Identifying unexpected behavior in device motion within the fluoroscopy FOV helps identify potentially unintended behavior occurring outside the fluoroscopy FOV. Another result of applying the first artificial intelligence and second artificial intelligence by the artificial intelligence controller 180 may be production of warnings when predicted and observed motion fall outside of a normal range of agreement. Warnings produced using the trained artificial intelligence implemented by the artificial intelligence controller 180 may help prevent the use of excess force at the proximal end of the interventional medical device 101 when expected motion is not observed at the distal end of the interventional medical device 101. This, in turn, will help prevent adverse events such as vessel dissection or perforation, pseudo-aneurysm, vessel spams, and other undesired outcomes such as accidental dislodging of parts of lesions, guidewire fracture, etc.

Although not shown, the control system 100 in FIG. 1 may also include a feedback controller to alert physicians when unexpected behavior outside the FOV is predicted. A feedback controller may produce warnings such as alarm sounds, a printed message on a fluoroscopy display, haptic feedback to the proximal end of the interventional medical device 101, or robotic control guidance. Robotic control guidance may be provided with displayed directions to modify motion at the proximal end of the interventional medical device 101. The displayed directions may include, for example, suggestions to move a robot control forward, backward, or laterally, suggestions on touchscreen or joystick motion for Corindus CorPath, suggestions on knob rotation for steerable sheaths, steerable guide catheters, or a transesophageal echocardiogram (TEE) probe. A feedback controller may also provide robotic control guidance in a closed loop system by, for example, sending commands to an autonomous robot to automatically pull back. A feedback controller may also provide robotic control guidance to a cooperative control robot to inhibit further forward motion if forward motion may be causing buckling.

Although the control system 100 is primarily described in the context of an X-ray imaging system, the control system 100 may include or be incorporated into interventional ultrasound imaging systems and both fixed and mobile interventional X-ray imaging systems. The control system 100 may be used for various fluoroscopy-based interventional medical procedures, including but not limited to interventional vascular procedures.

Figure 2:
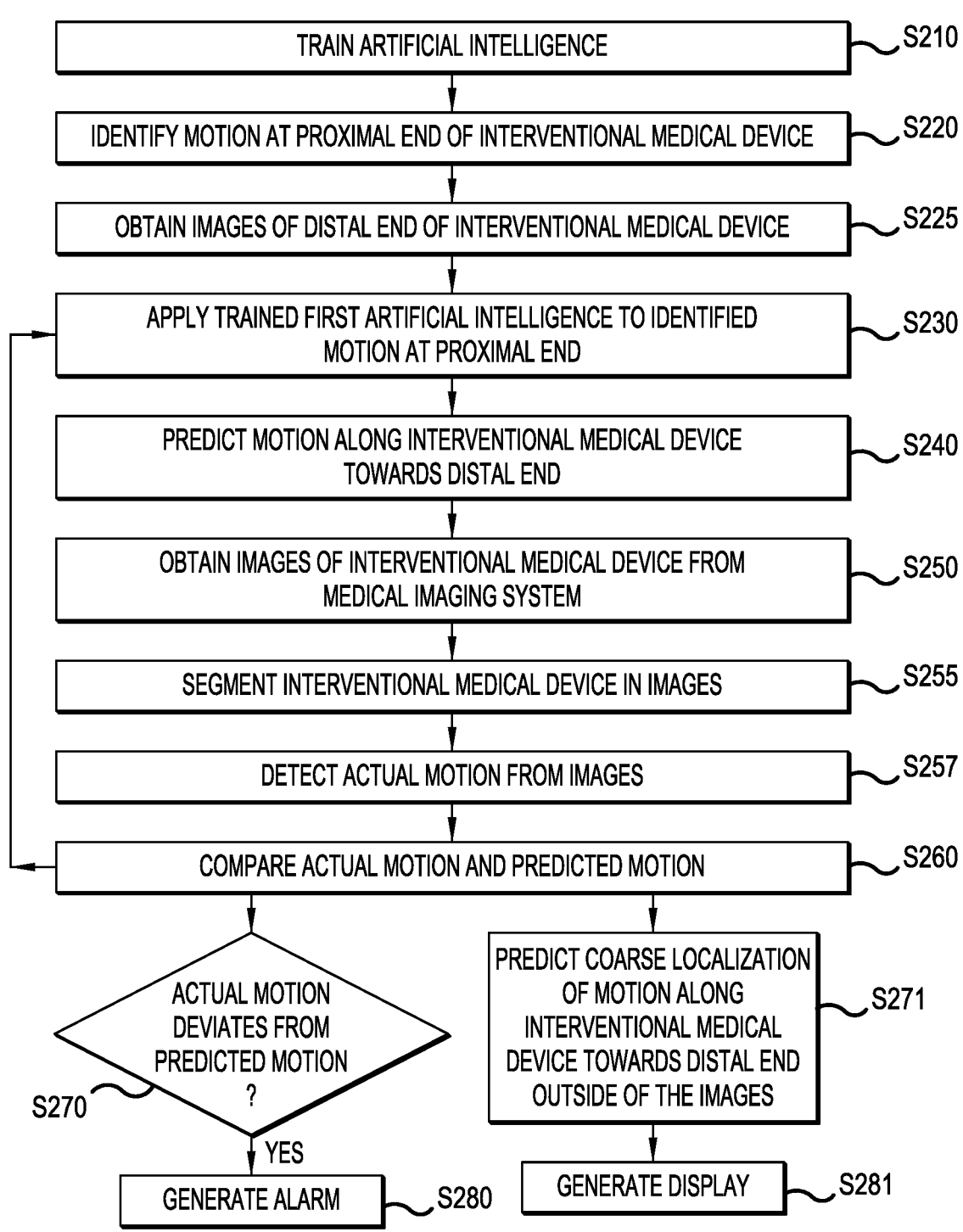
FIG. 2 illustrates a method for predictive motion mapping for flexible devices, in accordance with a representative embodiment.

FIG. 2 illustrates a method for predictive motion mapping for flexible devices, in accordance with a representative embodiment.

At S210, the method of FIG. 2 starts by training artificial intelligence. The trained artificial intelligence may include first artificial intelligence and second artificial intelligence which are trained using different inputs to produce different outputs. Additionally, the output from the first artificial intelligence may be an input to the second artificial intelligence. Moreover, a first prediction or projection from the first artificial intelligence may be output from the first artificial intelligence and input to the second artificial intelligence, and the second artificial intelligence may output a second prediction or projection based on using the first prediction or projection from the first artificial intelligence as an input. Ground truth information of coarse localizations of unexpected behavior of interventional medical devices may be used to train the artificial intelligence and the trained artificial intelligence may be used once the artificial intelligence is deployed. The features of the first artificial intelligence and second artificial intelligence are explained more in the paragraphs that follow. Training of the artificial intelligence at S210 may be performed entirely before the artificial intelligence is deployed. In one embodiment, adaptive artificial intelligence may use feedback after deployment for self-improvement via reinforcement learning or other learning methods.

The artificial intelligence controller 180 from FIG. 1 may implement the training of first trained artificial intelligence and second trained artificial intelligence. For example, in multiple training sessions for multiple interventional medical devices, the artificial intelligence controller 180 may input at least one location of the distal ends of the interventional medical devices, detect motion at proximal ends of the interventional medical devices, and detect motion along the interventional medical devices towards distal ends of the interventional medical devices resulting from the motion at the proximal ends of the interventional medical devices. In the multiple training sessions for multiple interventional medical devices, the artificial intelligence controller 180 may additionally be configured to input a type of an interventional medical device, a type of anatomy or procedure, or other contextual information that varies for different interventional medical procedures. The locations of the distal ends of the interventional medical devices in training may be obtained from images such as by being derived from medical images from a medical imaging system. The multiple training sessions may also include predicting, based on the at least one location of the distal ends of the interventional medical devices and the detected motion at the proximal ends of the interventional medical devices, predicted motion along the interventional medical devices towards distal ends of the interventional medical devices. The multiple training sessions may also include detecting the actual motion along the interventional medical devices towards the distal ends of the interventional medical devices, and determining losses based on differences between the predicted motion and the actual motion. The first trained artificial intelligence may establish a relationship between the motion at the proximal ends of the interventional medical devices and the motion along the interventional medical devices towards distal ends of the interventional medical devices, and the first artificial intelligence may be updated based on each loss determined based on differences between the predicted motion and the detected actual motion.

After the training at S210, the artificial intelligence may be provided for use. The first artificial intelligence may then be implemented by the artificial intelligence controller 180 in FIG. 1.

For the interventional medical procedure, the first artificial intelligence may additionally be trained for different types of interventional medical device 101. The first trained artificial intelligence may optionally input and act based on at least one of a type of the interventional medical device 101, a type of the interventional medical procedure, an anatomical landmark or at least one physical characteristic of a patient. A clinician may be provided with a drop-down menu to select a type of the interventional medical device 101. Predicted motion along the interventional medical device 101 towards the distal end of the interventional medical device 101 may be predicted based additionally on the selected interventional medical device type. Similarly, the predicting of the predicted motion may be additionally based on anatomy of a patient in the interventional medical procedure, a position of the medical imaging system, or a physical characteristic of the interventional medical device 101. Alternatively, the type of the interventional medical device 101 subjected to the first artificial intelligence may be automatically selected by performing object detection and classification before the interventional medical procedure, such as before the interventional medical device 101 is inserted into the patient. The detection and classification may be implemented based on images captured by operating room cameras. Alternatively, the detection and classification may be implemented using a model that is trained by machine learning to detect and classify different types of interventional medical devices. A training dataset for machine learning used to create a model may include training instances containing X-ray images of multiple different interventional medical devices. The training data may contain only normal or expected motion at the distal ends of the multiple different interventional medical devices, so that the artificial intelligence will learn to predict the normal motion at the distal ends of the different interventional medical devices, and during inference, if subsequent observed motion is not similar to predicted normal motion so that an alarm or alert can be generated and issued. Training data may be collected using shape sensing technology such as FORS. FORS provides 3D shape information along the length of the device and, therefore, allows confirmation that data contains expected motion and does not contain unexpected motion such as buckling, etc.

In operation during an interventional medical procedure, the first artificial intelligence may be implemented also based on additional context information such as target region or anatomy, segmentation of surrounding anatomy, pose of a C-arm along with target region to allow the first artificial intelligence to learn when to expect foreshortening. Additionally, the first artificial intelligence may receive constraints to the output such as length of the interventional medical device 101 in the fluoroscopy images, or maximum allowed curvature of the interventional medical device 101.

The first artificial intelligence may be a neural network such as a convolutional neural network, encoder-decoder network, generative adversarial network, capsule network, regression network, reinforcement learning agent, and may use motion information at the proximal end of the interventional medical device 101 and the fluoroscopy image at initial time t to predict motion or motion field along the length of the interventional medical device 101 visible in the fluoroscopy field of view (FOV). The observed motion or motion field between fluoroscopy images at time t and t+n may be compared with the motion predicted by the first artificial intelligence to learn the expected range of motion that may be observed in the fluoroscopy FOV. The time t+n may be after a particular motion at the proximal end is completed, or another arbitrary time such as when the particular motion at the proximal end is occurring. The predicted and observed (ground truth) motions are compared by computing a loss function such as mean square error, or mean absolute error, or Huber loss, or any loss that calculates difference between two motion vectors ($R^2$, $R^3$), for instance geodesic loss. Motion can be represented by vectorial parametrization and/or non-vectorial parametrization and/or motion fields. The parametrizations may be in the form of Euler angles, quaternions, a matrix, an exponential map, and/or angle-axis representing rotations and/or translations (e.g., including a direction and a magnitude for the translations and rotations)

At S220, the method of FIG. 2 includes identifying motion at a proximal end of the interventional medical device. Motion in the proximal end can include forward translation, lateral translation, and rotation along the axis. The motion in the proximal end is motion induced by a user or a robot, and may include any motion the user or robot induces to control the interventional medical device 101. Motion information at the proximal end of an interventional device may be obtained from a sensing device. Examples of a sensing device that can capture and provide such motion information includes a device tracker, an inertial measurement unit (IMU) sensor, a monocular or stereoscopic camera system serving as an optical tracking system, a linear encoder, torque encoders, or optical encoders. Examples of a device tracker include an optical tracking sensing system, an optical tracking system, an electromagnetic tracking system, or an optical shape sensing mechanism. Examples of an IMU sensor include a sensor that measures angular rate, force and possibly magnetic field, with components such as an accelerometer, gyroscope and possibly a magnetometer. Examples of a linear encoder include an optical linear encoder, a magnetic linear encoder, and a capacitive inductive linear encoder.

At S225, the method of FIG. 2 includes obtaining medical imagery of the interventional medical device. The medical imagery obtained at S225 may be obtained by the medical imaging system 120. The medical imagery obtained at S225 may be used to obtain at least one location of the distal end of the interventional medical device 101 from images of the distal end of the interventional medical device 101. The medical imagery may be fluoroscopy images of the part of the interventional medical device within the field of view of the medical imaging system. The medical imagery obtained at S225 is of part of the interventional medical device towards the distal end. Embodiments based on FIG. 2 include obtaining images of the distal end of the interventional medical device before S230, such as when segmented representations of the interventional medical device are used as inputs to the first artificial intelligence applied at S230. In FIG. 4B which is discussed later, the image(s) of the distal end are represented as the fluoroscopy frame $f_r$. The medical imagery may include single or time-series fluoroscopy images containing the distal end of the interventional medical device 101. The medical imagery may be automatically segmented by an image processing controller using methods such as thresholding, template matching, active contour modeling, multiscale ridge enhancement filters, or deep learning based segmentation algorithms.

At S230, the method of FIG. 2 includes applying trained first artificial intelligence to the identified motion at the proximal end of the interventional medical device and the medical image of the distal end of the interventional medical device at the time that motion is applied to the proximal end of the interventional medical device. The trained first artificial intelligence is artificial intelligence trained to find correlations between the motion applied at the proximal end of the interventional medical device and motion received at the distal end of the interventional medical device which is observed in interventional medical imagery.

At S240, the first artificial intelligence predicts motion along the interventional medical device towards the distal end based on the motion identified at the proximal end of the interventional medical device 101 at S220 and images of the interventional medical device toward the distal end at S225. The first artificial intelligence may be implemented by receiving fluoroscopy images of a segmented representation of the interventional medical device covering images of the interventional medical device 101 initially without unexpected/unintended behavior such as buckling at S225. Since the first artificial intelligence has been trained before the interventional medical procedure, the first artificial intelligence may use the initial information of the interventional medical device from the segmented representation as a basis for determining normal or expected proximal-to-distal motion mapping.

At S250, the method of FIG. 2 includes obtaining images of the interventional medical device from a medical imaging system. The images of the interventional medical device obtained at S250 may be images of the distal end of the interventional medical device and/or towards the distal end of the interventional medical device.

At S255, the method of FIG. 2 includes segmenting the interventional medical device in the images from the medical imaging system. The segmenting results in a segmented representation of the interventional medical device. S255 may be optional and may also be performed on images of the interventional medical device towards the distal end that are obtained at S225 and that are input into the trained first artificial intelligence at S230.

At S257, actual motion is detected from the images from the medical imaging system.

At S260, the detected actual motion of the interventional medical device is compared to predicted motion of the interventional medical device. The predicted motion of the interventional medical device compared at S260 in FIG. 2 is the motion predicted at S240.

At S270, a determination is made whether the actual motion deviates from the predicted motion. The deviation may be identified from a binary classification process, or may be based on one or more thresholds, scoring algorithms, or other processes that determine whether the actual motion of the interventional medical device is within expectations from the predicted motion.

If the actual motion does not deviate from the predicted motion (S270=No), no alarm is generated. If the actual motion deviates from the predicted motion (S270=Yes), an alarm is generated at S280.

Additionally, at S271, the method of FIG. 2 includes predicting the coarse localization of motion along the interventional medical device outside the field of view of the images from the interventional medical device. Additionally, the second artificial intelligence may predict a predicted confidence in the predicted coarse localization. The coarse localization predicted at S271 may be predicted by the second artificial intelligence described herein. The second artificial intelligence may be implemented by the artificial intelligence controller 180, and implements a localization neural network. The second artificial intelligence is configured to receive the predicted device motion and observed device motion from fluoroscopy images. Data to train the second artificial intelligence at S210 to predict coarse localization of motion occurring outside the FOV of the medical imaging system may be obtained using shape sensing technologies such as FORS.

The second artificial intelligence may be implemented by a trained neural network such as a convolutional neural network, encoder-decoder network, generative adversarial network, capsule network, regression network, reinforcement learning agent. The second artificial intelligence may use as inputs the predicted motion and observed motion at the distal end to predict if and where unexpected and/or unintended behavior such as buckling is occurring outside the fluoroscopy FOV, and compares its prediction with ground truth information of a ground truth localization obtained in training at S210 such as from FORS. The predicted localization and the ground truth localization from the ground truth information are compared by computing a loss function such as mean square error, or mean absolute error, or Huber loss, and so forth. The second artificial intelligence may produce warnings if unexpected/unintended behavior is predicted. Warnings may be produced based on presence or absence of unintended behavior predicted in the manner described herein.

At S281, a display is generated for the predicted coarse localization along the interventional medical device outside the FOV of the images.

Figure 3:
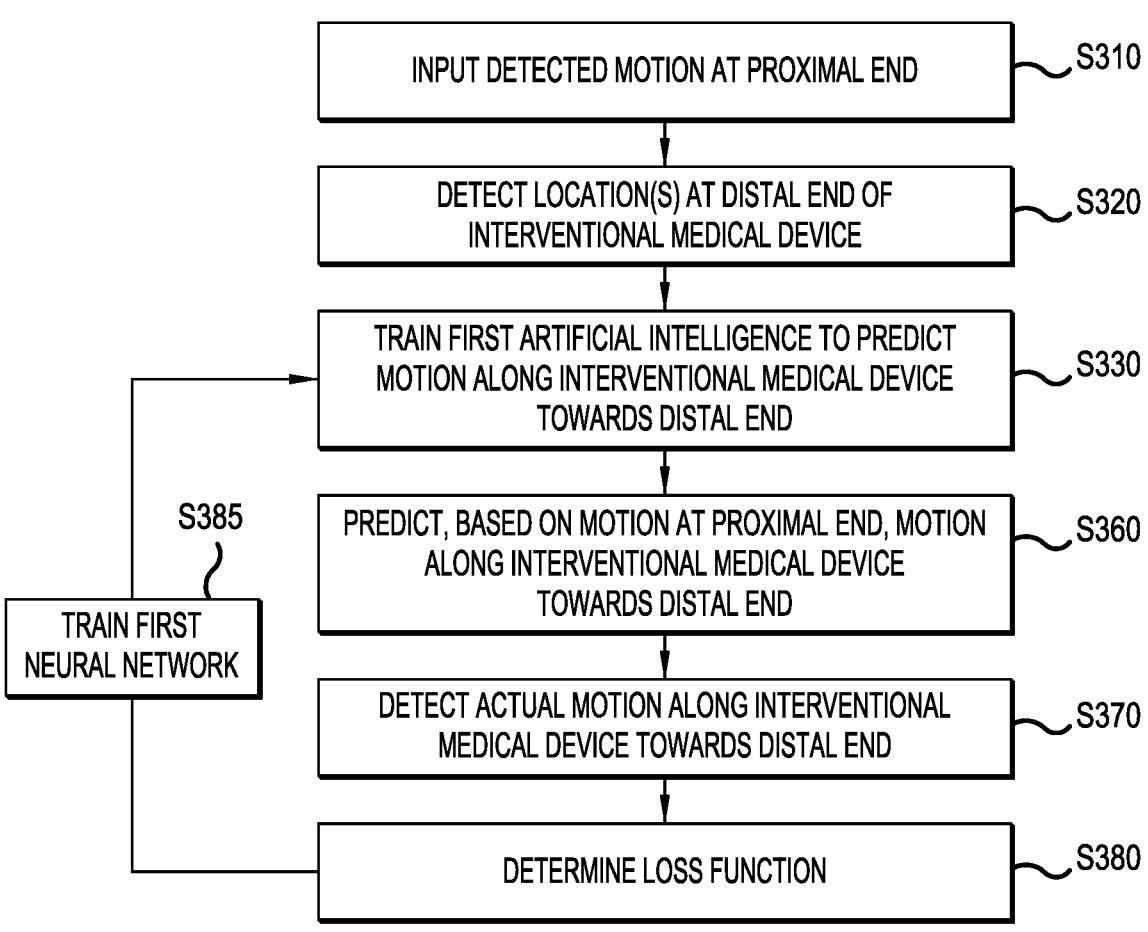
FIG. 3 illustrates another method for predictive motion mapping for flexible devices, in accordance with another representative embodiment.

FIG. 3 illustrates another method for predictive motion mapping for flexible devices, in accordance with another representative embodiment.

At S310, the method of FIG. 3 includes inputting detected motion at a proximal end of an interventional medical device.

At S320, at least one location of the distal ends of the interventional medical device is detected.

At S330, first artificial intelligence is trained to predict motion along the interventional medical device towards the distal end.

At S360, motion along the interventional medical device towards the distal end is predicted based on the motion at the proximal end and the medical image of the distal end of the interventional medical device prior to application of motion at the proximal end of the interventional medical device.

At S370, actual motion along the interventional medical device towards the distal end is detected. The actual motion is detected from a medical image of or a segmented representation of the part of the interventional medical device within the field of view of the medical imaging system.

At S380, the method of FIG. 3 includes determining a loss function based on the difference between the predicted motion and the actual motion toward the distal end of the interventional medical device.

At S385, the first neural network is updated based on the determined loss function, and the process returns to S330.

In the embodiment of FIG. 3, the first neural network may be updated at S385 as the first neural network is trained. In an embodiment, if the data generated during an operation represents normal or expected proximal-to-distal motion mapping and can be reliably used as a ground truth, then the first neural network may be updated at S385 using this data after the first neural network is in operation.

Figure 4A:
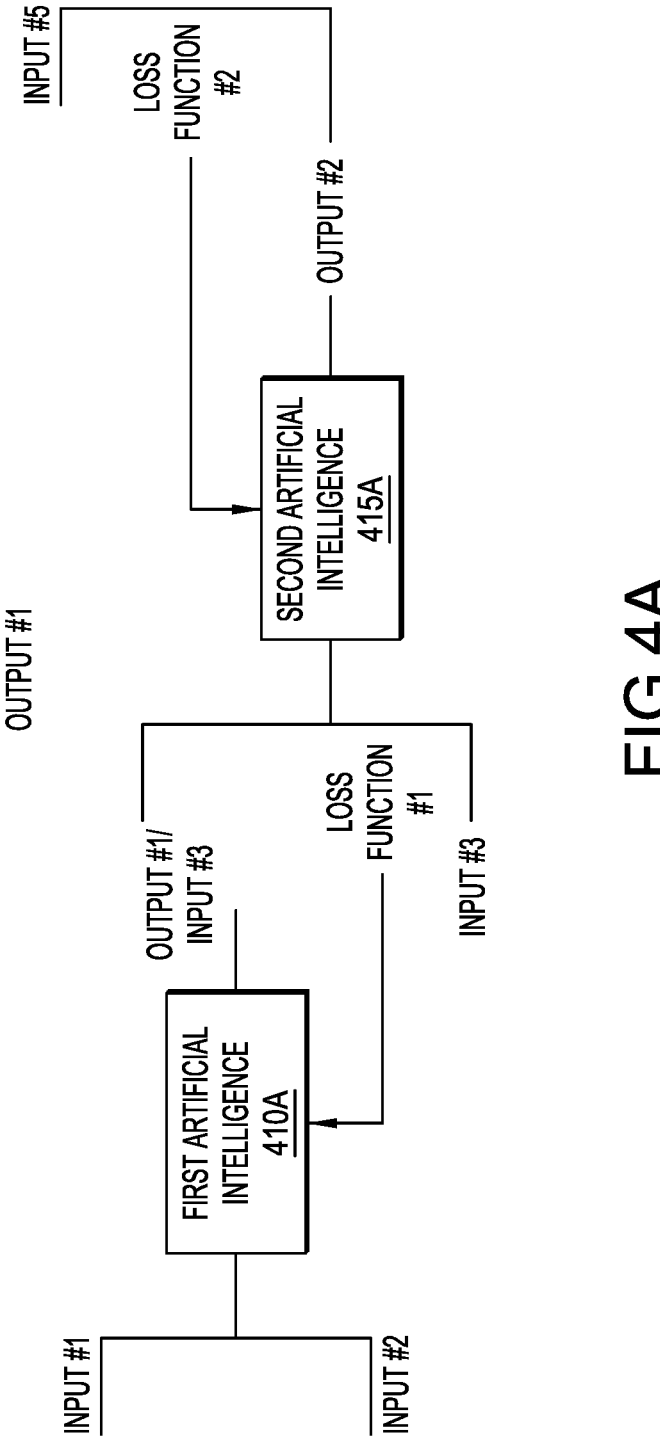
FIG. 4A illustrates a hybrid process for predictive motion mapping for flexible devices, in accordance with a representative embodiment.
Figure 4B:
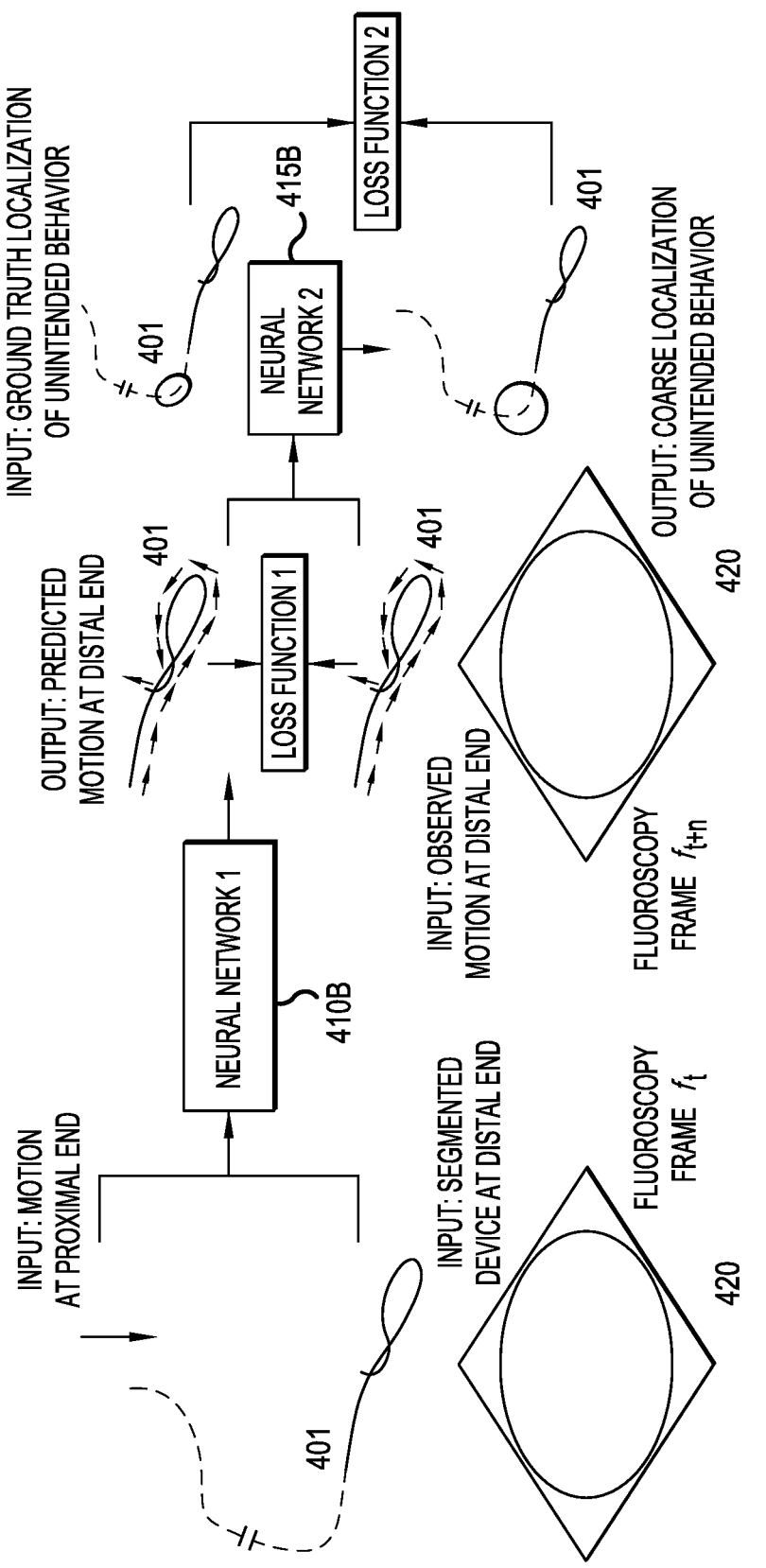
FIG. 4B illustrates another hybrid process for predictive motion mapping for flexible devices, in accordance with a representative embodiment.

FIG. 4A illustrates a hybrid process for predictive motion mapping for flexible devices, in accordance with a representative embodiment.

In FIG. 4A, first artificial intelligence 410A and second artificial intelligence 415A are trained using a first loss function (loss function #1) and a second loss function (loss function #2) based on inputs that include motion at the proximal end and the distal end of an interventional medical device. The inputs to the first artificial intelligence 410A and to the second artificial intelligence 415A during training are explained by way of example for the corresponding features of FIG. 4B as explained below.

FIG. 4B illustrates another hybrid process for predictive motion mapping for flexible devices, in accordance with a representative embodiment.

In FIG. 4B, a proximal-to-distal predictive motion mapping process and system is schematically represented. An interventional medical device 401 such as a guidewire and a medical imaging system 420 such as fluoroscopic X-ray medical imaging system are used to train artificial intelligence such as in a controlled environment. The interventional medical device 401 may include a first region that is visible in medical imaging and a second region that is not visible in medical imaging. The first region and the second region may vary in operation as the FOV of the medical imaging system 420 varies. During an operation, the first region and the second region may change as the view of the medical imaging changes. First artificial intelligence may be trained to establish a relationship between motion at a proximal end of an interventional medical device 401 and resultant motion at the distal end of the interventional medical device 401 by using the motion at the proximal end of the interventional medical device 101 and the medical image of the distal end of the interventional medical device 101 at the time that motion is applied to the proximal end of the interventional medical device 101, and predicting the resultant motion at the distal end and then comparing it to observed motion at the distal end. Second artificial intelligence may be trained using the observed motion and the predicted motion at the distal end to predict a coarse localization of unintended behavior of the interventional medical device 401 and comparing the predicted coarse localization of unintended behavior to a ground truth coarse localization of the unintended behavior. The training of the second neural network 415B may use ground truth information of coarse localizations of distal ends of interventional medical devices, so that learning from the training may be used once the second neural network 415B is deployed.

In FIG. 4B, a segmentation of the interventional medical device 401 in a fluoroscopy frame, $f_r$, 420 is provided as input to a first neural network 410B along with the motion applied at the proximal end of the interventional medical device 401. To be sure, the segmentation of the interventional medical device 401 in FIG. 4B is for a first region that includes the part of the interventional medical device 401 in the field of view (FOV) in the medical imaging system. Another part of the interventional medical device 401 is not within the field of view (FOV) in the medical imaging system. The first neural network 410B outputs point-wise motion estimates along the length of the segmented representation of the interventional medical device 401. The point-wise motion estimates are compared against observations computed from the segmented representation of the interventional medical device 401 at a later fluoroscopy frame, $f_{r+n}$. In other words, the first neural network 410B in FIG. 4B learns the correlation of how motion at the proximal end of the interventional medical device 401 results in motion at points along the distal end of the interventional medical device 401.

Also in FIG. 4B, the predicted point-wise motion estimates along the length of the segmented representation of the interventional medical device and the actual motion observed from the segmented representations are input to a second neural network 415B. To be sure, the inputs to the second neural network 415B are for the estimated and actual motion of the interventional medical device 401 in the first region that includes the part of the interventional medical device 401 in the field of view (FOV) in the medical imaging system. The output of the second neural network 415B is a prediction of the coarse localization of unintended motion in the second region that includes the part of the interventional medical device 401 outside the field of view of the medical imaging system. The estimated coarse localization in the second region is compared against ground truth localization in the second region as obtained from a mechanism such as shape sensing technology. For example, the ground truth localization may be obtained via shape sensing technology such as Fiber Optic RealShape (FORS) from Philips Corporation.

As described above, in FIG. 4B a first neural network 410B is trained to output point-wise motion estimates along the length of the interventional medical device 401 towards the distal end based on inputs of the motion at the proximal end of the interventional medical device 401 and the segmented representation of the interventional medical device 401. The training of the first neural network 410B is based on feeding back a first loss function (loss function 1) reflecting the difference between the predicted motion and the observed motion at the distal end of the interventional medical device 401. The second neural network 415B is trained to output a coarse localization of unintended behavior of the interventional medical device 401 based on the point-wise motion estimates and actual observable motion within the field of view of the medical imaging system. The training of the second neural network 415B is based on feeding back a second loss function (loss function 2) reflecting the difference between the output of the coarse localization and the ground truth localization of unintended behavior. During the training in FIG. 4B, the predicted coarse localization of the unintended behavior may be confirmed via a second loss function using an actual localization from, for example, optical shape sensing. The use of the predicted localization during training may be applied during operation even when actual localization is not used once the second neural network is trained to an acceptable accuracy. As a result, unintended behavior of the interventional medical device 401 can be predicted and coarsely localized.

Figure 5:
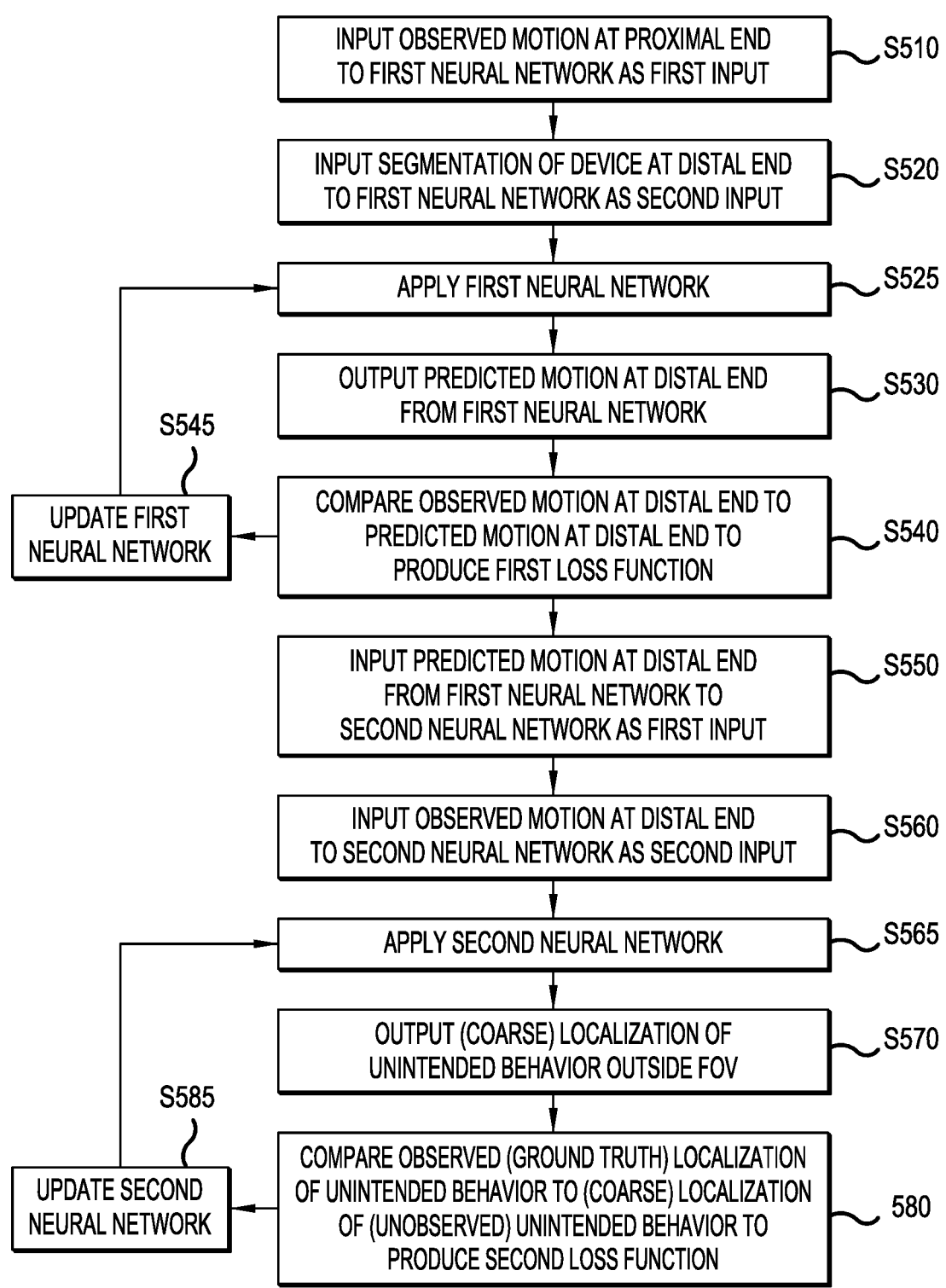
FIG. 5 illustrates a method for predictive motion mapping for flexible devices, in accordance with a representative embodiment.

FIG. 5 illustrates a method for predictive motion mapping for flexible devices, in accordance with a representative embodiment.

In FIG. 5, training of the first artificial intelligence and the second artificial intelligence is described. At S510, observed motion at a proximal end of an interventional medical device is input to a first neural network as first input.

At S520, segmentation of the interventional medical device at the distal end is input to the first neural network as second input.

At S525, the first neural network is applied to the inputs from S510 and S520.

At S530, predicted motion at the distal end of the interventional medical device is outputted from the first neural network.

At S540, observed motion at the distal end of the interventional medical device is compared to predicted motion at the distal end of the interventional medical device to produce a first loss function.

At S545, the first neural network is updated. The process of training the first neural network continues by returning to S525 until the process ends.

At S550, predicted motion at the distal end of the interventional medical device from the output of the first neural network is input to the second neural network as first input.

At S560, observed motion at the distal end of the interventional medical device is input to the second neural network as second input.

At S565, the second neural network is applied.

At S570, a coarse localization of unintended behavior outside the field of view of the imaging device is output by the second neural network At S580, ground truth localization of the unintended behavior of the interventional medical device is compared to the predicted coarse localization of unintended behavior to produce a second loss function.

At S585, the second loss function is fed back to update the second neural network. After S585, the process of training the second neural network returns to S565.

Figure 6A:
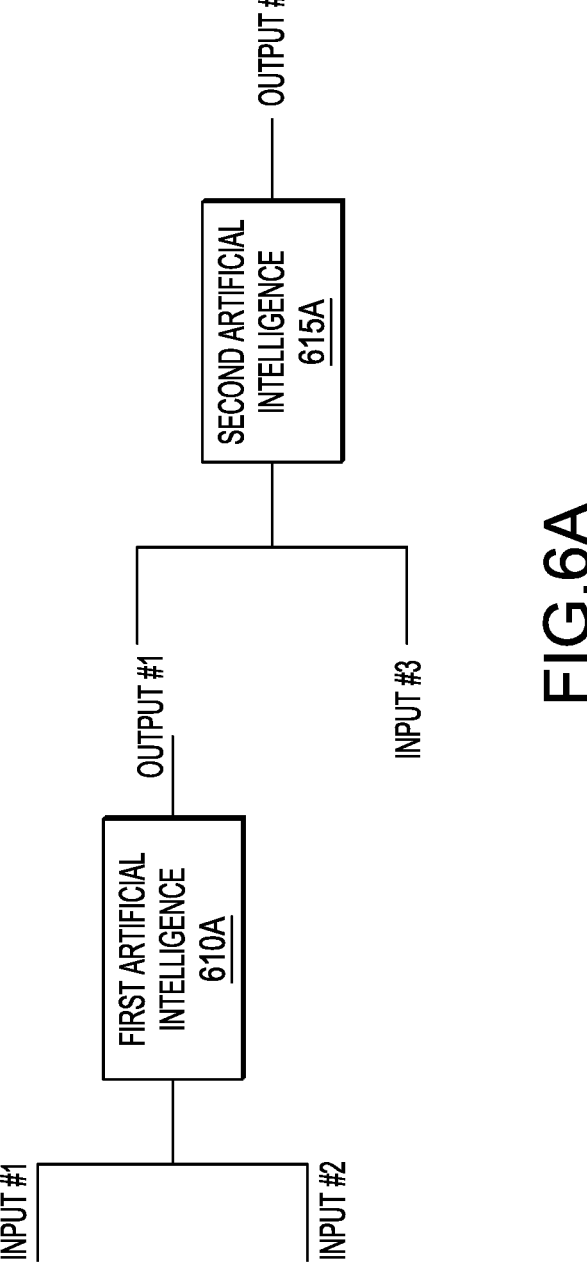
FIG. 6A illustrates a hybrid process for predictive motion mapping for flexible devices, in accordance with a representative embodiment.

FIG. 6A illustrates a hybrid process for predictive motion mapping for flexible devices, in accordance with a representative embodiment.

In FIG. 6A, first artificial intelligence 610A and second artificial intelligence 615A are used in operation to produce outputs as described herein. The inputs to the first artificial intelligence 610A and to the second artificial intelligence 615A during operation are explained by way of example for the corresponding features of FIG. 6B as explained below.

Figure 6B:
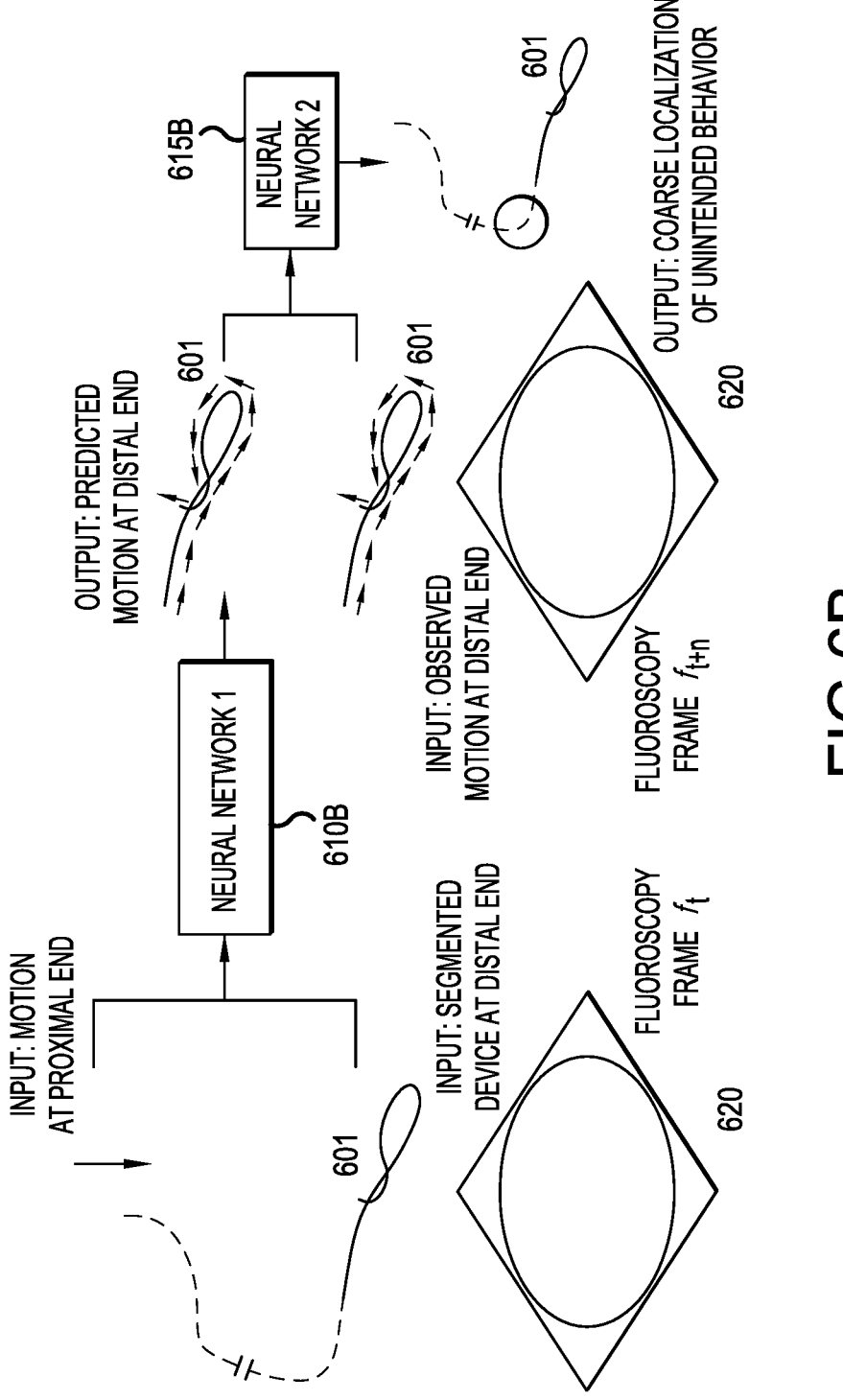
FIG. 6B illustrates another hybrid process for predictive motion mapping for flexible devices, in accordance with a representative embodiment.

FIG. 6B illustrates another hybrid process for predictive motion mapping for flexible devices, in accordance with a representative embodiment.

In FIG. 6B, another proximal-to-distal predictive motion mapping process and system is schematically represented. The hybrid process and system in FIG. 6B may be used during an interventional medical procedure. As in the hybrid process of FIG. 6B, for any fluoroscopy frame, $f_t$, a segmentation of the interventional medical device 601 in a first region within the field of view of the medical imaging is provided as input to a first neural network 610B along with the motion applied at the proximal end of the interventional medical device 601. The first neural network 610B outputs point-wise motion estimates along the length of the segmented representation of the interventional medical device 601. The estimates from the first neural network 610B are compared against observations computed from the segmented representation of the interventional medical device 601 in the first region within the field of view of the medical imaging system at a later fluoroscopy frame, $f_{t+n}$. The two motions, estimated and observed, become inputs to a second neural network 616B that predicts coarse localization of where unintended motion in the second region outside the fluoroscopy FOV might be, when the two motions do not match.

FIG. 6C illustrates a method for predictive motion mapping for flexible devices, in accordance with a representative embodiment.

In FIG. 6C, observed motion at a proximal end of an interventional medical device is input to a first neural network as first input at S610.

At S620, a segmentation of the interventional medical device at a distal end of the interventional medical device is input to the first neural network as second input. The segmented representation may be provided as binary masks of segmented representations of the interventional medical device in fluoroscopy images.

At S625, the first neural network is applied to the first input at S610 and second input at S620.

At S630, predicted motion at the distal end of the interventional medical device is output from the first neural network as predicted motion. The first neural network may be a trained encoder-decoder network. The predicted motion may be motion along the length of the interventional medical device toward the distal end and may be output by the trained encoder-decoder network.

At S650, predicted motion at the distal end of the interventional medical device which is output from the first neural network is input to the second neural network as a first input.

At S660, observed motion at a distal end of the interventional medical device is input to the second neural network as second input. The second neural network may be a trained convolutional neural network.

At S665, the second neural network is applied to the predicted motion at S650 and the observed motion at S660.

At S670, the second neural network outputs a coarse localization of unintended behavior outside the FOV of the medical imaging system. The second neural network may localize unexpected/unintended behavior in the interventional medical device 101 outside the fluoroscopy FOV based on disagreement between predicted and observed motion at the distal end of the interventional medical device within the FOV of the medical imaging system. The prediction may be used to generate an alarm as describe above.

As described in embodiments above, one or more deep learning algorithm(s) are trained to learn the relationship or mapping between motion applied at the proximal end of an interventional medical device and the motion observed at the distal end of the interventional medical device. The captured input motion may include manual motion or mechanical motion such as robotic motion or robot assisted motion, and may be rotation and/or translation. In alternative embodiments, the deep learning algorithm(s) may also learn proximal-to-distal mapping of a velocity field at multiple points, acceleration, inertia, spatial configuration, tangential (angular) motion and linear velocity or acceleration. The learning by the deep learning algorithm(s) may take into account specific parameters of the interventional medical device. During a procedure, the control system 100 estimates the motion of an interventional medical device at the distal end, given the motion applied to the interventional medical device at the proximal end and the medical image of the distal end of the interventional medical device at the time that motion is applied to the proximal end of the interventional medical device. The control system 100 may also learn to relate the differences in predicted and observed device motion at the distal end to different unobserved device behaviors occurring outside the fluoroscopy FOV. The control system 100 may then alert physicians about possible unintended behavior in the interventional medical device outside the FOV of the medical imaging system and, therefore, prevent possible vessel damage or other undesired outcomes.

In an embodiment, consistent with the teachings above, a deep learning model may be trained to predict motion at the distal end of an interventional medical device 101 from two-dimensional coordinates of the segmented representation of the interventional medical device 101 or from two-dimensional coordinates of spline fit to the segmented representation of the interventional medical device in a fluoroscopy view.

In another embodiment, a recurrent neural network (RNN) architecture such as a long short-term memory (LSTM) network, a temporal convolutional network (TCN), or a transformer, for example, may be used to observe the segmented representation of the interventional medical device 101 in multiple fluoroscopy frames (t_0 to t_n) to better inform the motion prediction in frame t_n.

In another embodiment, a deep learning model may be trained to predict the location(s) of the segmented representation of the interventional medical device in frame t_(n+1) from segmentation of the interventional medical device in either only frame t_n or in frames t_0 to t_n. The prediction may be directly compared to the observed device in fluoroscopy frame t_(n+1).

In another embodiment, a three-dimensional model or a set of parameters, rules, or characteristics of the known interventional medical device 101 is used to inform predictions of motion or velocity of the interventional medical device 101.

In another embodiment, a deep learning algorithm may be trained to learn the proximal-to-distal mapping of device-specific parameters. Examples of device-specific parameters include velocity field over multiple points, acceleration, inertia, spatial configuration, tangential/angular and linear velocity or acceleration. Predicted parameters may be compared against measured parameters in this embodiment.

In another embodiment, a machine learning algorithm may use the predicted and observed motion information to classify the observation as normal or abnormal. Examples of a machine learning algorithm include a one-class support vector machine (SVM) classifier or deep learning based classifier. In this embodiment, when an anomaly is detected a warning may be produced.

In another embodiment, a deep learning network may be trained to predict motion at the distal end of an interventional medical device from ultrasound images of the distal end of the interventional medical device. The input to the deep learning network may be provided from ultrasound images, a binary mask of a segmented representation of the interventional medical device in ultrasound, two-dimensional (x,y) coordinates of the segmented representation of the interventional medical device 101 in ultrasound, or a two-dimensional (x,y) coordinates of a spline fit to the segmented representation of the interventional medical device 101 in ultrasound.

In yet another embodiment, a deep learning network may be trained to additionally learn the confidence in the predicted motion at the distal end of the interventional medical device based on agreement with ground truth during training or any other method of determining confidence or uncertainty. The control system 100 may learn the types of input motion at the proximal end of the interventional medical device 101 that produce confident estimates at the distal end, or the type of fluoroscopy views that are associated with confident motion predictions. For example, the control system 100 may learn that a view showing foreshortening may not produce very confident motion estimates at the distal end. Confidence in the predicted motion at the distal end predicted by a first deep learning network may additionally be input into a second network to predict the coarse localization of unintended behavior along the interventional medical device 101 outside the field of view of the medical imaging system. Similarly, the second deep learning network may be trained to additionally predict the confidence in the predicted coarse localization of unintended behavior along the interventional medical device 101 outside the field of view of the medical imaging system.

In still another embodiment, an endovascular robotic system measures the force being applied at the tip of a catheter to either display the measurements of force on the console or incorporate the measurements of force into the control loop. This feature may alert the clinician to the danger of continued force and, therefore, decrease the likelihood of perforation or other damage to the vessel wall. In this embodiment, detection of abnormal or unintended device behavior such as buckling is incorporated into either the safety mechanisms or the control loop of the robotic system. For instance, if buckling is predicted at the end-effector (distal part), the risk of vessel wall perforation is high, and robotic actuators will decelerate or the emergency stop will be triggered. The user may be notified on the console and asked to perform a corrective action. Alternatively, the control system 100 may automatically withdraw the end-effector, steer it to a different orientation, and re-approach the cannulation in the case of semi- or fully-autonomous robots. If buckling occurs in the medical part of the guidewire, the control system 100 will adjust the settings of the controller 150 such as PID controller parameters including gain and motor velocities in the background using either preprogrammed rules or complex predictive models. The user may only be notified when the controller adjustments fail or are ineffective, thus avoiding operator overload, cognitive burden, and lowered trust in the robotic system. Robotics systems may also learn the preferences of the operators and notify them only when buckling occurs in certain areas, with certain intensity or frequency, or for certain durations.

In yet another embodiment, complex input at the proximal end of an interventional medical device 101 in the form of touchscreen or joystick manipulations such as to control Corindus CorPath, or knob rotations such as to control steerable sheaths, steerable guide catheters, TEE probe, are incorporated. If the control system 100 detects unintended behavior in the interventional medical device, the control system 100 may suggest mechanisms to eliminate unintended behavior in the context of the input device. Examples of an input device include a touchscreen, a joystick and a knob.

Figure 7:
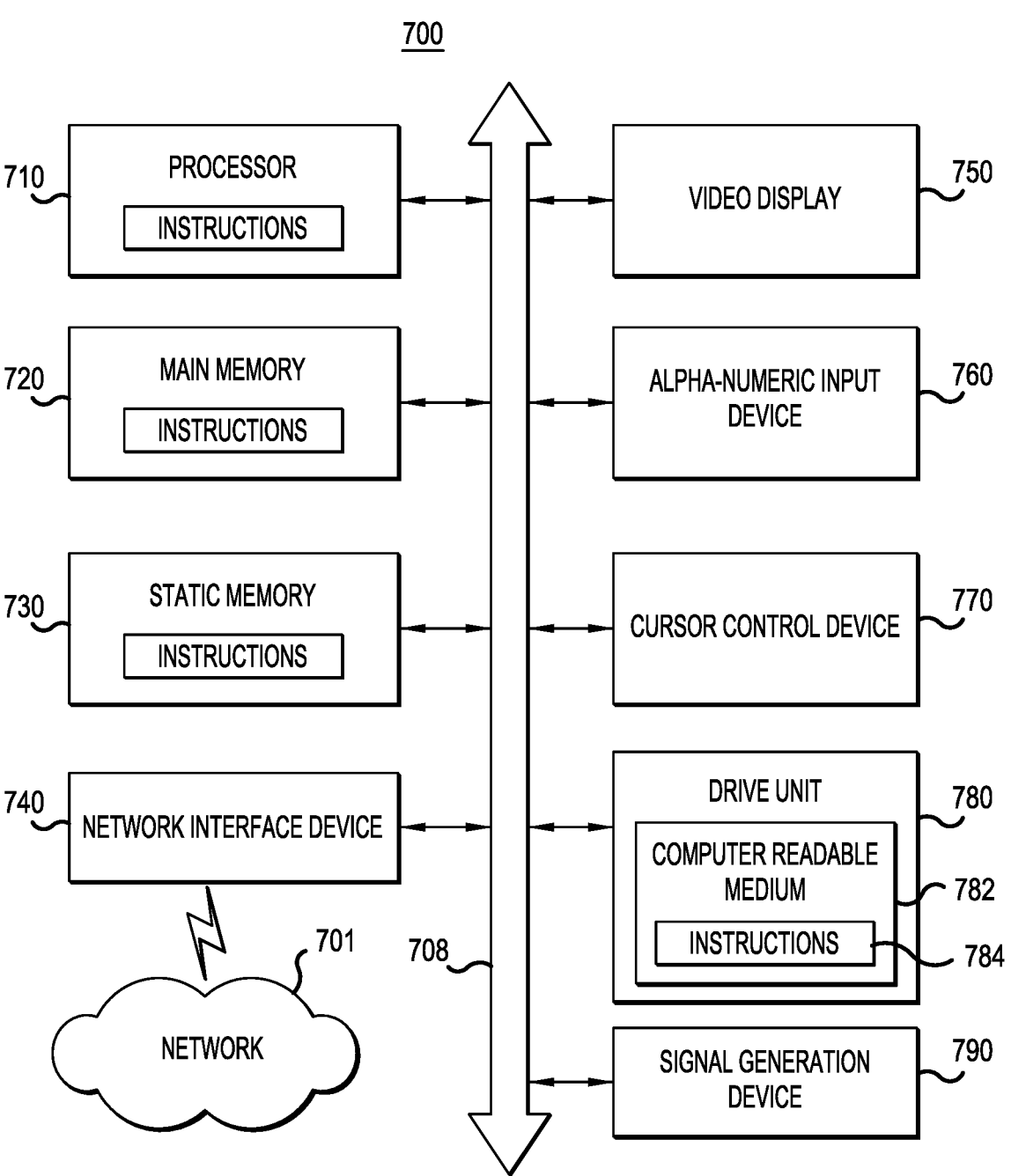
FIG. 7 illustrates a computer system, on which a method for predictive motion mapping for flexible devices is implemented, in accordance with another representative embodiment.

FIG. 7 illustrates a computer system, on which a method for predictive motion mapping for flexible devices is implemented, in accordance with another representative embodiment.

The computer system 700 of FIG. 7 shows a complete set of components for a communications device or a computer device. However, a "controller" as described herein may be implemented with less than the set of components of FIG. 7, such as by a memory and processor combination. The computer system 700 may include some or all elements of one or more component apparatuses in a system for predictive motion mapping for flexible devices herein, although any such apparatus may not necessarily include one or more of the elements described for the computer system 700 and may include other elements not described.

Referring to FIG. 7, the computer system 700 includes a set of software instructions that can be executed to cause the computer system 700 to perform any of the methods or computer-based functions disclosed herein. The computer system 700 may operate as a standalone device or may be connected, for example, using a network 701, to other computer systems or peripheral devices. In embodiments, a computer system 700 performs logical processing based on digital signals received via an analog-to-digital converter.

In a networked deployment, the computer system 700 operates in the capacity of a server or as a client user computer in a server-client user network environment, or as a peer computer system in a peer-to-peer (or distributed) network environment. The computer system 700 can also be implemented as or incorporated into various devices, such as the controller 150 in FIG. 1, a stationary computer, a mobile computer, a personal computer (PC), a laptop computer, a tablet computer, or any other machine capable of executing a set of software instructions (sequential or otherwise) that specify actions to be taken by that machine. The computer system 700 can be incorporated as or in a device that in turn is in an integrated system that includes additional devices. In an embodiment, the computer system 700 can be implemented using electronic devices that provide voice, video or data communication. Further, while the computer system 700 is illustrated in the singular, the term "system" shall also be taken to include any collection of systems or sub-systems that individually or jointly execute a set, or multiple sets, of software instructions to perform one or more computer functions.

As illustrated in FIG. 7, the computer system 700 includes a processor 710. The processor 710 may be considered a representative example of the processor 152 of the controller 150 in FIG. 1 and executes instructions to implement some or all aspects of methods and processes described herein. The processor 710 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The processor 710 is an article of manufacture and/or a machine component. The processor 710 is configured to execute software instructions to perform functions as described in the various embodiments herein. The processor 710 may be a general-purpose processor or may be part of an application specific integrated circuit (ASIC). The processor 710 may also be a microprocessor, a microcomputer, a processor chip, a controller, a microcontroller, a digital signal processor (DSP), a state machine, or a programmable logic device. The processor 710 may also be a logical circuit, including a programmable gate array (PGA), such as a field programmable gate array (FPGA), or another type of circuit that includes discrete gate and/or transistor logic. The processor 710 may be a central processing unit (CPU), a graphics processing unit (GPU), tensor processing unit (TPU), or some combination. Additionally, any processor described herein may include multiple processors, parallel processors, or both. Multiple processors may be included in, or coupled to, a single device or multiple devices.

The term "processor" as used herein encompasses an electronic component able to execute a program or machine executable instruction. References to a computing device comprising "a processor" should be interpreted to include more than one processor or processing core, as in a multi-core processor. A processor may also refer to a collection of processors within a single computer system or distributed among multiple computer systems. The term computing device should also be interpreted to include a collection or network of computing devices each including a processor or processors. Programs have software instructions performed by one or multiple processors that may be within the same computing device or which may be distributed across multiple computing devices.

The computer system 700 further includes a main memory 720 and a static memory 730, where memories in the computer system 700 communicate with each other and the processor 710 via a bus 708. Either or both of the main memory 720 and the static memory 730 may be considered representative examples of the memory 151 of the controller 150 in FIG. 1, and store instructions used to implement some or all aspects of methods and processes described herein. Memories described herein are tangible storage mediums for storing data and executable software instructions and are non-transitory during the time software instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The main memory 720 and the static memory 730 are articles of manufacture and/or machine components. The main memory 720 and the static memory 730 are computer-readable mediums from which data and executable software instructions can be read by a computer (e.g., the processor 710). Each of the main memory 720 and the static memory 730 may be implemented as one or more of random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. The memories may be volatile or non-volatile, secure and/or encrypted, unsecure and/or unencrypted.

"Memory" is an example of a computer-readable storage medium. Computer memory is any memory which is directly accessible to a processor. Examples of computer memory include, but are not limited to RANI memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

As shown, the computer system 700 further includes a video display unit 750, such as a liquid crystal display (LCD), an organic light emitting diode (OLED), a flat panel display, a solid-state display, or a cathode ray tube (CRT), for example. Additionally, the computer system 700 includes an input device 760, such as a keyboard/virtual keyboard or touch-sensitive input screen or speech input with speech recognition, and a cursor control device 770, such as a mouse or touch-sensitive input screen or pad. The computer system 700 also optionally includes a disk drive unit 780, a signal generation device 790, such as a speaker or remote control, and/or a network interface device 740.

In an embodiment, as depicted in FIG. 7, the disk drive unit 780 includes a computer-readable medium 782 in which one or more sets of software instructions 784 (software) are embedded. The sets of software instructions 784 are read from the computer-readable medium 782 to be executed by the processor 710. Further, the software instructions 784, when executed by the processor 710, perform one or more steps of the methods and processes as described herein. In an embodiment, the software instructions 784 reside all or in part within the main memory 720, the static memory 730 and/or the processor 710 during execution by the computer system 700. Further, the computer-readable medium 782 may include software instructions 784 or receive and execute software instructions 784 responsive to a propagated signal, so that a device connected to a network 701 communicates voice, video or data over the network 701. The software instructions 784 may be transmitted or received over the network 701 via the network interface device 740.

In an embodiment, dedicated hardware implementations, such as application-specific integrated circuits (ASICs), field programmable gate arrays (FPGAs), programmable logic arrays and other hardware components, are constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing may implement one or more of the methods or functionalities as described herein, and a processor described herein may be used to support a virtual processing environment.

Accordingly, predictive motion mapping for flexible devices provides guidance as to actual positioning of interventional medical devices, such as when the interventional medical devices are used in interventional medical procedures under the guidance of live two-dimensional fluoroscopy imaging. Characteristics of the interventional medical devices that may lead to unintended motion can be used as a basis for compensating the unintended motion. Similarly, anatomy of patients that may lead to unintended motion can be used as a basis for compensating the unintended motion.

This invention describes a system that learns the range of motions or behaviors that can be expected at the distal end, given particular motions or actions at the proximal end and a current position or configuration of the distal end of the interventional medical device. The system can then predict expected motions along the length of the guidewire visible in fluoroscopy and raise alerts when observed motions are outside the range of expected motions. Further, the system can observe the type of unexpected motion in the fluoroscopy field of view (FOV) and predict where unexpected or unintended behavior outside the fluoroscopy FOV is occurring, for instance, close to the FOV or away from it.

Nevertheless, predictive motion mapping for flexible devices is not limited as an application to specific details described herein, and instead is applicable to additional embodiments in which one or more inputs to the first artificial intelligence and the second artificial intelligence vary from the specific details described for embodiments herein.

Although predictive motion mapping for flexible devices has been described with reference to several exemplary embodiments, it is understood that the words that have been used are words of description and illustration, rather than words of limitation. Changes may be made within the purview of the appended claims, as presently stated and as amended, without departing from the scope and spirit of predictive motion mapping for flexible devices in its aspects. Although predictive motion mapping for flexible devices has been described with reference to particular means, materials and embodiments, predictive motion mapping for flexible devices is not intended to be limited to the particulars disclosed; rather predictive motion mapping for flexible devices extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

We claim:

1. A controller for interventional medical devices, the controller comprising:
a memory configured to store instructions, and
a processor configured to execute the instructions, and, when executed by the processor, the instructions cause the controller to:
obtain at least one location of a distal end of an interventional medical device during an interventional medical procedure;
identify motion at a proximal end of the interventional medical device during the interventional medical procedure;
predict, based on the motion at the proximal end of the interventional medical device and the at least one location of the distal end of the interventional medical device, motion along the interventional medical device towards the distal end of the interventional medical device during the interventional medical procedure;
obtain images of the distal end of the interventional medical device from a medical imaging system;
compare, from the images of the interventional medical device, actual motion along the interventional medical device towards the distal end of the interventional medical device and predicted motion along the interventional medical device towards the distal end of the interventional medical device;
determine a deviation of the actual motion from the predicted motion; and
predict, based on the actual motion and the predicted motion, coarse localization of unintended behavior along the interventional medical device outside of a field of view of the medical imaging system.

2. The controller of claim 1, wherein, when executed by the processor, the instructions further cause the controller to:
obtain the at least one location of the distal end of the interventional medical device from images of the distal end of the interventional medical device from the medical imaging system; and
predict the predicted motion along the interventional medical device towards the distal end of the interventional medical device for a plurality of locations along the interventional medical device towards the distal end of the interventional medical device.

3. The controller of claim 1, wherein, when executed by the processor, the instructions cause the controller to:

input, to a first trained artificial intelligence model, the identified motion at the proximal end of the interventional medical device, the at least one location of the distal end of the interventional medical device, and at least one of: a type of the interventional medical device, a type of the interventional medical procedure, an anatomical landmark, or at least one physical characteristic of a patient, and
predict the predicted motion along the interventional medical device towards the distal end of the interventional medical device by application of the first trained artificial intelligence model.

4. The controller of claim 1, wherein, when executed by the processor, the instructions further cause the controller to:
generate an alarm in response to the deviation of the actual motion from the predicted motion.

5. A system for controlling interventional medical devices, the system comprising:
a sensor configured to detect motion at a proximal end of an interventional medical device; and
a controller comprising a memory configured to store instructions and a processor configured to execute the instructions, and, when executed by the processor, the instructions cause the controller to:
obtain at least one location of a distal end of an interventional medical device during an interventional medical procedure;
identify the motion at the proximal end of the interventional medical device during the interventional medical procedure;
predict, based on the identified motion at the proximal end of the interventional medical device and the at least one location of the distal end of the interventional medical device, motion along the interventional medical device towards the distal end of the interventional medical device during the interventional medical procedure;
obtain images of the distal end of the interventional medical device from a medical imaging system;
compare, from the images of the interventional medical device, actual motion along the interventional medical device towards the distal end of the interventional medical device and predicted motion along the interventional medical device towards the distal end of the interventional medical device;
determine a deviation of the actual motion from the predicted motion; and
an artificial intelligence controller configured to implement a first trained artificial intelligence model and a second trained artificial intelligence model, and, when executed by a second processor, second instructions cause the artificial intelligence controller to:
in a plurality of training sessions for a plurality of interventional medical devices, input at least one location of distal ends of the interventional medical devices, identify motion at proximal ends of the interventional medical devices, and detect actual motion along the interventional medical devices towards distal ends of the interventional medical devices resulting from the motion at the proximal ends of the interventional medical devices;
predict, based on the at least one location of the distal ends of the interventional medical devices and the identified motion at the proximal ends of the interventional medical devices, motion along the interventional medical device towards the distal ends of the interventional medical devices;

determine losses based on differences between the predicted motion and the actual motion;

establish, by the first trained artificial intelligence model, a relationship between the motion at the proximal ends of the interventional medical devices and the motion along the interventional medical devices towards distal ends of the interventional medical devices, and update the first trained artificial intelligence model based on each loss determined based on differences between the predicted motion and the actual motion.

6. The system of claim 5, further comprising:

the medical imaging system, and wherein, when executed by the processor, the instructions further cause the controller to:

obtain the at least one location of the distal end of the interventional medical device from images of the distal end of the interventional medical device from the medical imaging system; and segment the images from the medical imaging system to identify the interventional medical device imaged by the medical imaging system.

7. The system of claim 5, wherein, when executed by the second processor, the second instructions cause the artificial intelligence controller further to:

input, in a plurality of training sessions, ground truth information of coarse localizations of the interventional medical devices outside of fields of view of the medical imaging system;

predict, based on the predicted motion and the actual motion, and by applying the second artificial intelligence model, coarse localizations of the interventional medical devices outside of the fields of view of the medical imaging system; and determining losses based on differences between the ground truth information of the coarse localizations of the interventional medical devices and the predicted coarse localizations of the interventional medical devices outside of the fields of view of the medical imaging system; and update the second artificial intelligence model based on each loss.

8. The system of claim 5, further comprising:

a robot configured to control motion at the proximal end of the interventional medical device; and an interface configured to output an alert based on the predicted motion along the interventional medical device towards the distal end of the interventional medical device inside a field of view of the medical imaging system.

9. The system of claim 5, wherein, when executed by the processor, the instructions further cause the controller to:

apply a first artificial intelligence model trained to predict the motion along the interventional medical device towards the distal end of the interventional medical device based on input of the identified motion at the proximal end of the interventional medical device and the at least one location of the distal end of the interventional medical device.

10. The system of claim 9, wherein the first artificial intelligence model is trained to predict the motion along the interventional medical device towards the distal end of the interventional medical device based further on input of at least one of a type of the interventional medical device, a type of the interventional medical procedure, an anatomical landmark, or at least one physical characteristic of a patient.

11. A method for controlling interventional medical devices, the method comprising:

obtaining at least one location of a distal end of the interventional medical device from a medical imaging system during an interventional medical procedure;

identifying motion at a proximal end of an interventional medical device during the interventional medical procedure;

predicting, based on the identified motion at the proximal end of the interventional medical device and the at least one location of the distal end of the interventional medical device, motion along the interventional medical device towards the distal end of the interventional medical device during the interventional medical procedure;

obtaining images of the distal end of the interventional medical device from a medical imaging system;

comparing, from the images of the interventional medical device, actual motion along the interventional medical device towards the distal end of the interventional medical device and predicted motion along the interventional medical device towards the distal end of the interventional medical device;

determining a deviation of the actual motion from the predicted motion;

predicting, based on the actual motion and the predicted motion, coarse localization of unintended behavior along the interventional medical device outside of a field of view of the medical imaging system; and generating a display of the predicted coarse localization of unintended behavior along the interventional medical device outside of the field of view of the medical imaging system.

12. The method of claim 11, further comprising:

segmenting the images of the interventional medical device to identify the interventional medical device imaged by the medical imaging system.

13. The method of claim 11, further comprising:

predicting the predicted motion based on at least one of a type of the interventional device, anatomy of a patient in the interventional medical procedure, a position of the medical imaging system, or a physical characteristic of the interventional medical device; and outputting an alarm based on the deviation of the actual motion from the predicted motion.

14. The method of claim 11, further comprising:

applying a first artificial intelligence model trained to predict the motion along the interventional medical device towards the distal end of the interventional medical device based on input of the identified motion at the proximal end of the interventional medical device and the at least one location of the distal end of the interventional medical device.

15. The method of claim 14, wherein the first artificial intelligence model is trained to predict the motion along the interventional medical device towards the distal end of the interventional medical device based further on input of at least one of a type of the interventional medical device, a type of the interventional medical procedure, an anatomical landmark, or at least one physical characteristic of a patient.

16. A method for controlling interventional medical devices, the method comprising:

obtaining at least one location of a distal end of the interventional medical device from a medical imaging system during an interventional medical procedure;

identifying motion at a proximal end of an interventional medical device during the interventional medical procedure;

predicting, based on the identified motion at the proximal end of the interventional medical device and the at least one location of the distal end of the interventional medical device, motion along the interventional medical device towards the distal end of the interventional medical device during the interventional medical procedure;

obtaining images of the distal end of the interventional medical device from a medical imaging system;

comparing, from the images of the interventional medical device, actual motion along the interventional medical device towards the distal end of the interventional medical device and predicted motion along the interventional medical device towards the distal end of the interventional medical device;

determining a deviation of the actual motion from the predicted motion;

predicting the predicted motion along with a confidence in the predicted motion; and predicting, based on the actual motion, the predicted motion, and the confidence in the predicted motion, coarse localization of unintended behavior along the interventional medical device outside of a field of view of the medical imaging system and a predicted confidence in the predicted coarse localization.

17. A system for controlling interventional medical devices, the system comprising:

a sensor configured to detect motion at a proximal end of an interventional medical device; and a controller comprising a memory configured to store instructions and a processor configured to execute the instructions, and, when executed by the processor, the instructions cause the controller to:

obtain at least one location of a distal end of an interventional medical device during an interventional medical procedure;

identify the motion at the proximal end of the interventional medical device during the interventional medical procedure;

predict, based on the identified motion at the proximal end of the interventional medical device and the at least one location of the distal end of the interventional medical device, motion along the interventional medical device towards the distal end of the interventional medical device during the interventional medical procedure;

obtain images of the distal end of the interventional medical device from a medical imaging system;

compare, from the images of the interventional medical device, actual motion along the interventional medical device towards the distal end of the interventional medical device and predicted motion along the interventional medical device towards the distal end of the interventional medical device;

determine a deviation of the actual motion from the predicted motion;

apply a first artificial intelligence model trained to predict the motion along the interventional medical device towards the distal end of the interventional medical device based on input of the identified motion at the proximal end of the interventional medical device and the at least one location of the distal end of the interventional medical device; and apply a second artificial intelligence model trained to predict coarse localization of unintended behavior along the interventional medical device outside of a field of view of the medical imaging system based on input of the actual motion and the predicted motion.

\* \* \* \* \*